United States Patent [19]
Berry, Jr.

[11] Patent Number: 5,279,800
[45] Date of Patent: Jan. 18, 1994

[54] DENTAL CASSETTE KIT

[75] Inventor: Bernie B. Berry, Jr., Indianapolis, Ind.

[73] Assignee: C/T Med-Systems Ltd., Inc., Indianapolis, Ind.

[21] Appl. No.: 981,617

[22] Filed: Nov. 25, 1992

[51] Int. Cl.⁵ .................... A61L 2/00; B01J 19/32; B65D 85/20; B65D 85/62

[52] U.S. Cl. ..................... 422/300; 422/297; 422/310; 206/363; 206/369; 206/370; 206/373

[58] Field of Search ............... 422/104, 297, 300, 310; 206/210, 263, 363, 369, 370, 373, 438, 480, 483, 565, 63.5, 591

[56] References Cited

U.S. PATENT DOCUMENTS

| | | | |
|---|---|---|---|
| D. 295,074 | 4/1988 | Jerge et al. | D24/9 |
| D. 295,075 | 4/1988 | Jerge et al. | D24/9 |
| 857,240 | 6/1907 | Henning | |
| 3,285,409 | 11/1966 | Loran | 206/63.5 |
| 3,532,221 | 10/1970 | Kaluhiokalani et al. | 211/60 |
| 3,589,511 | 6/1971 | Britt | 206/65 |
| 3,634,937 | 1/1972 | Green | 32/1 |
| 3,890,096 | 6/1975 | Nichol et al. | 21/105 |
| 3,982,630 | 9/1976 | Garnier | 206/369 |
| 4,191,291 | 3/1980 | Brown | 206/369 |
| 4,353,694 | 10/1982 | Pelerin | 433/77 |
| 4,541,992 | 9/1985 | Jerge et al. | 422/300 |
| 4,572,371 | 2/1986 | Asenbauer | 206/443 |
| 4,643,303 | 2/1987 | Arp et al. | 206/370 |
| 4,696,401 | 9/1987 | Wallace | 206/591 |
| 4,762,688 | 8/1988 | Berry, Jr. | 422/310 |
| 4,774,063 | 9/1988 | Runnells | 422/297 |
| 4,798,292 | 1/1989 | Hauze | 206/439 |
| 4,852,738 | 8/1989 | Craig et al. | 206/369 |
| 4,854,475 | 8/1989 | Riihimaki et al. | 220/337 |
| 4,938,360 | 7/1990 | Wallace | 206/591 |
| 4,959,199 | 9/1990 | Brewer | 422/300 |
| 5,004,418 | 4/1991 | Porteous | 433/77 |
| 5,084,251 | 1/1992 | Thomas | 422/300 |
| 5,098,676 | 3/1992 | Brooks, Jr. | 422/292 |

*Primary Examiner*—James C. Housel
*Assistant Examiner*—Rachel Freed
*Attorney, Agent, or Firm*—Woodard, Emhardt, Naughton, Moriarty & McNett

[57] ABSTRACT

An autoclavable cassette for the receipt and storage of dental and surgical instruments includes a metal tray portion including a base, four sides and two outwardly extending flanges and a metal lid portion which covers the open tray portion and assembles to the outwardly extending latches by means of a cooperating latch and pin combination. The metal cassette tray is configured with a variety of slots, apertures and pins which are used to receive customizing components so that the dentist or surgeon can, by his own selection of specific component options create his own customized cassette. Some of the customizing options include a generally rectangular rack which sets in and can be lifted out of the tray and which includes a series of aligned receiving channels for the receipt of dental or surgical instruments. Another customizing option includes a finger mat which fits within the tray with a snap-in/snap-out feature, providing greater versatility. A third customizing option is a metal storage box which can assume a variety of configurations and is used for smaller or irregularly shaped parts. In one variation of the preferred embodiment, two storage racks can be used in a stacked configuration so as to increase the capacity of the dental cassette.

6 Claims, 4 Drawing Sheets

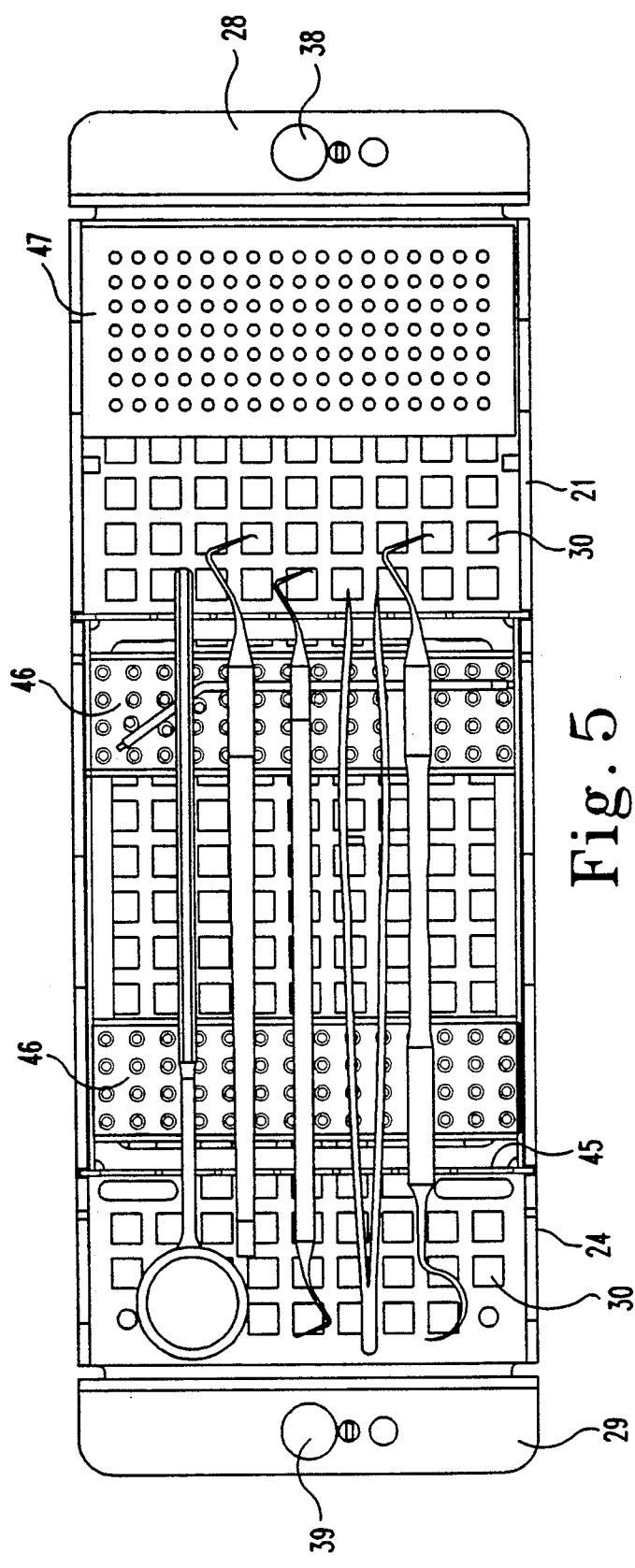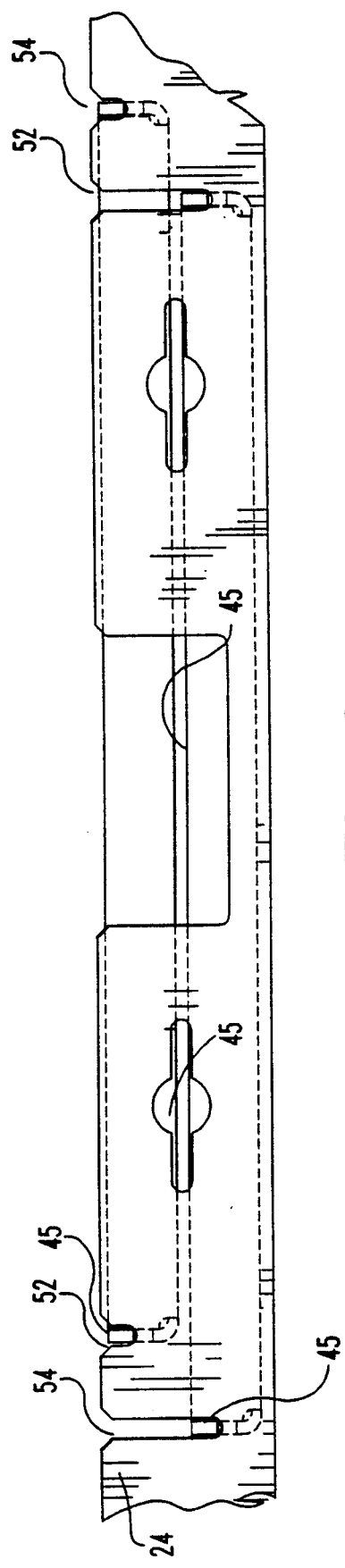
Fig. 5
Fig. 6

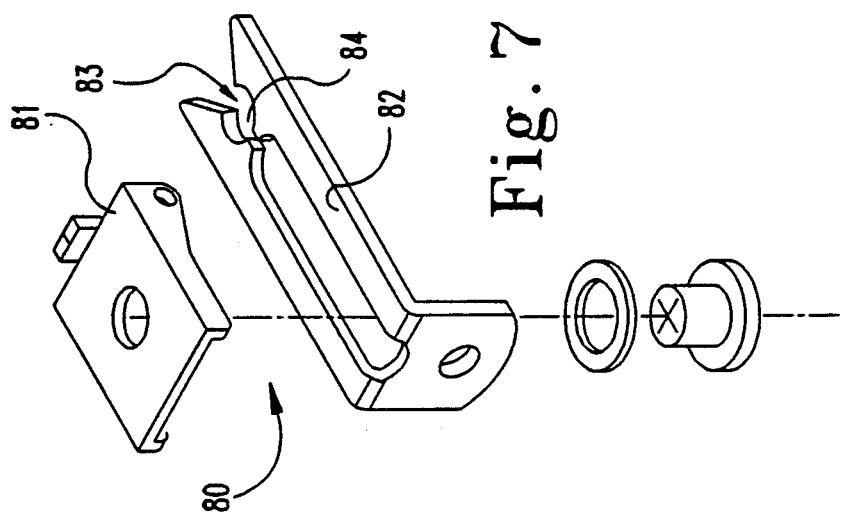
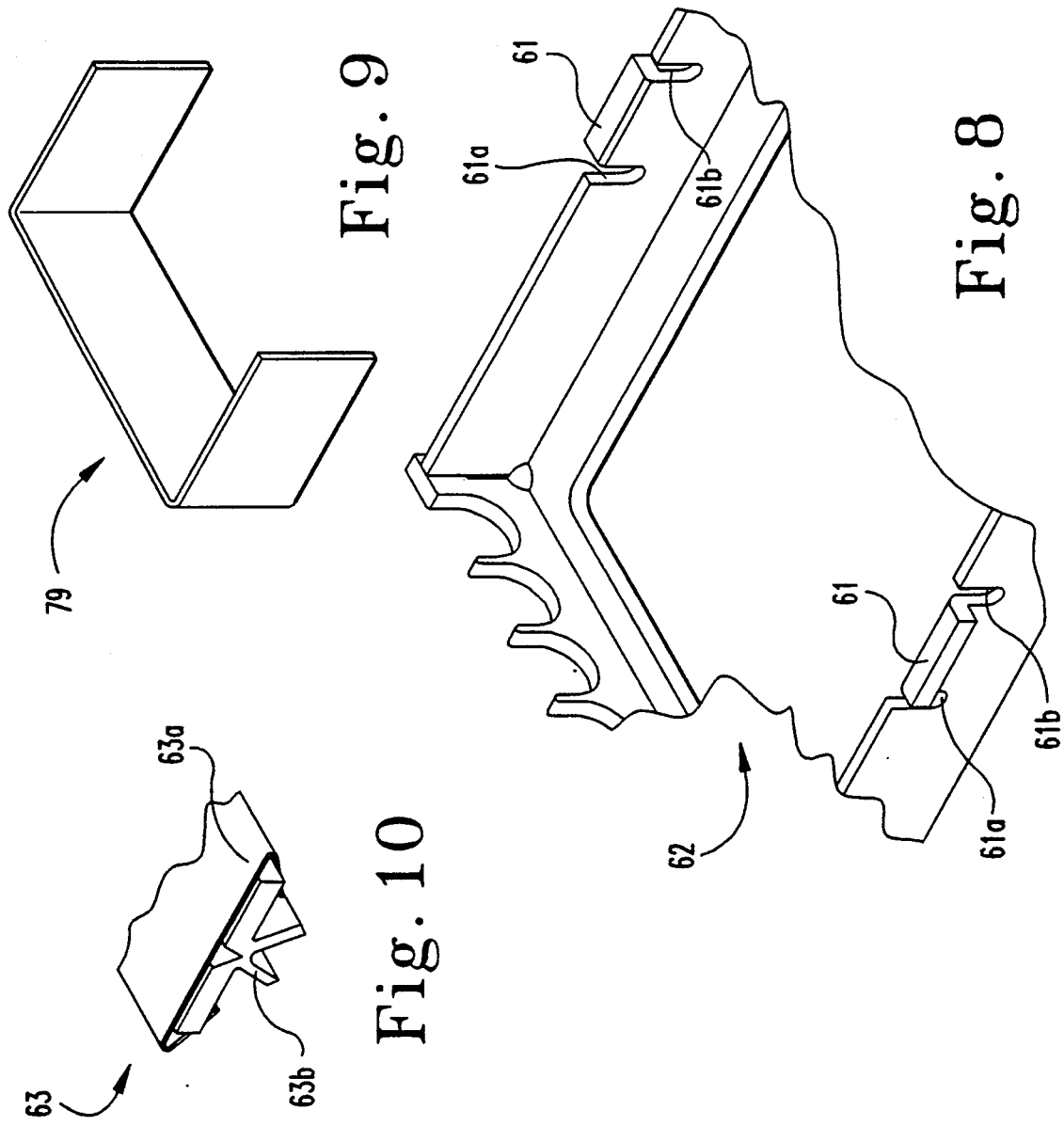

DENTAL CASSETTE KIT

BACKGROUND OF THE INVENTION

The present invention relates generally to autoclave cassettes which are used to retain and store surgical and dental instruments and appliances. More particularly the present invention relates to a dental cassette kit which permits the dentist to customize the kit construction by the selection of available kit components. While the focus of the present invention is on a dental cassette kit, the customizing features and selectable components are also applicable to surgical cassettes.

The design of dental and surgical cassettes which are intended for autoclaving have a number of common or typical features. For example, the materials which are used are selected to withstand the higher temperatures of autoclaving and steam holes are provided in the tray and lid portions for the flow of autoclaving steam in and around the instruments and appliances which are loaded into the cassette. These cassettes typically have some arrangement of hinges and/or latches in order to join the tray and lid together. The typical construction also includes some style of holder or retaining means for the instruments and appliances which are to be autoclaved.

The following patent references are believed to provide a representative sampling of the typical autoclave cassettes which have been generally described:

| Patent No. | Patentee | Date Issued |
| --- | --- | --- |
| 5,004,418 | Porteous | April 2, 1991 |
| 3,634,937 | Green | January 18, 1972 |
| 4,854,475 | Riihimaki et al. | August 8, 1989 |
| 3,890,096 | Nichol et al. | June 17, 1975 |
| 857,240 | Henning | June 18, 1907 |
| 3,285,409 | Loran | November 15, 1966 |
| 3,589,511 | Britt | June 29, 1971 |
| 5,098,676 | Brooks, Jr. | Mar. 24, 1992 |

Additionally, related autoclave cassette and enclosure designs are disclosed in my prior and co-pending patent applications, Ser. No. 07/954,563 filed Sep. 30, 1992 and Ser. No. 07/935,157 filed Aug. 25, 1992.

While these various cassette designs provide a variety of features and while they each attempt to address different concerns, they each have a fixed configuration. Once the designer or manufacturer decides on what the product configuration should be, that is what it is. The only choice the dentist or surgeon has as to the cassette style is limited to what someone else has already decided the dentist or surgeon would like. If the available cassettes do not offer quite what the dentist or surgeon would like to have as features and styling, the dentist or surgeon must sacrifice and compromise.

What is missing in these earlier cassette designs is the ability of the dentist/surgeon to customize his or her own cassette so as to provide greater versatility and the exact style desired. The present invention provides this customizing option by means of an autoclave cassette kit wherein the tray is machined with assembly features to receive a variety of retaining racks, finger mats and boxes.

As used herein the phrase "finger mats" encompasses a single unit as well as an assembly as typified by the preferred embodiment.

Each option item is easily assembled and disassembled from the tray so that an assortment of options can be separately purchased and used to customize the tray back and forth into a number of different configurations. With the standardized tray and lid, one cassette can be customized for a variety of procedures and instead of buying and stocking a number of fixed-style cassettes, a fewer number are required as they can be converted to different styles, interchangeably.

SUMMARY OF THE INVENTION

An autoclavable cassette for the receipt and storage of dental and surgical instruments according to one embodiment of the present invention comprises a tray portion, a lid portion, a lift out instrument rack, a finger mat and a storage box. The tray portion includes a base and four sidewalls which define an open interior space with two oppositely disposed ones of the sidewalls including rack slots and mat slots for receipt of the instrument rack and for receipt of the finger mat. The lid portion includes means for attaching the lid to the tray portion so as to enclose the interior space. The lift out instrument rack includes a plurality of receiving channels for receipt of a plurality of dental or surgical instruments. The finger mat includes a plurality of flexible fingers for receipt of at least one instrument which is wedged in between a plurality of the fingers. The storage box includes a lid which may be opened and closed for access to the interior and the storage box is placed in the tray portion of the cassette. A three-sided partition is an option in place of the storage box.

One object of the present invention is to provide an improved dental cassette kit.

Related objects and advantages of the present invention will be apparent from the following description.

BRIEF DESCRIPTION OF THE DRAWINGS

FIG. 5 is a top plan view of the FIG. 1 tray with the FIGS. 2-4 components installed and dental instruments loaded in place according to the present invention.

FIG. 6 is a partial, side elevational view of two FIG. 2 racks loaded in a stacked configuration into the FIG. 1 tray according to the present invention.

FIG. 7 is an exploded, perspective view of a latch mechanism used to secure the FIG. 1 lid and tray together.

FIG. 8 is a partial perspective view of an alternative lift-out instrument storage rack designed to be installed in the FIG. 1 cassette according to the present invention.

FIG. 9 is a perspective view of a partitioning bracket designed to be installed in the FIG. 1 cassette according to the present invention.

FIG. 10 is a partial perspective view of a hold-down strip attached to the FIG. 1 lid.

DESCRIPTION OF THE PREFERRED EMBODIMENT

Figure 1:
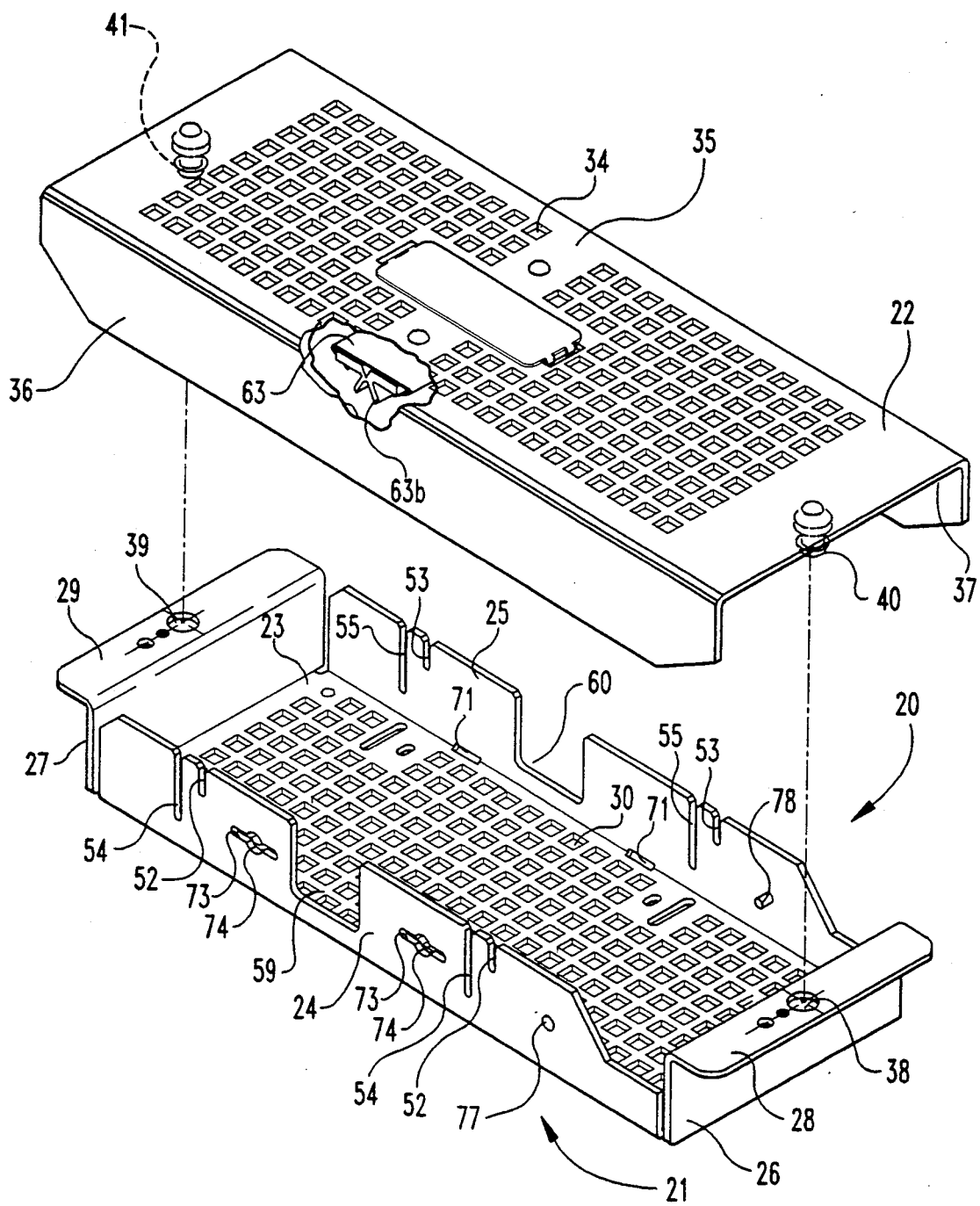
FIG. 1 is an exploded perspective view of a dental cassette according to the present invention with the tray and lid separated.
Figure 2:
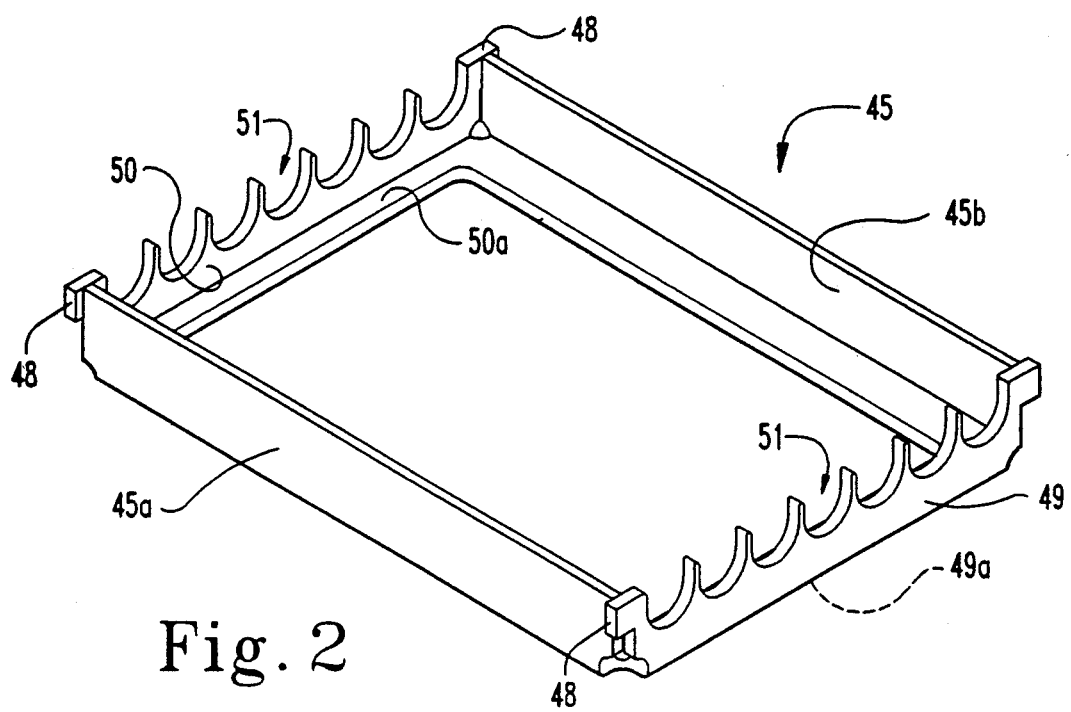
FIG. 2 is a perspective view of an instrument storage rack designed to be installed in the FIG. 1 cassette according to the present invention.
Figure 2A:
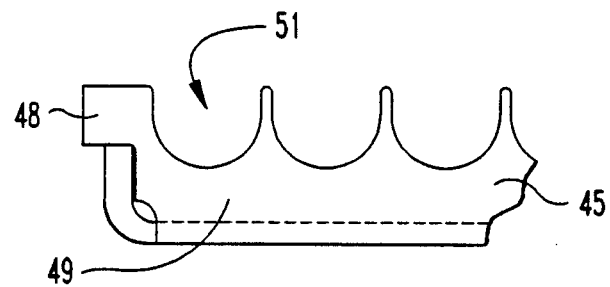
FIG. 2A is a partial side elevational view of the FIG. 2 storage rack showing a mounting support tab.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1 there is illustrated a dental cassette 20 including a tray 21 and cooperating lid 22. Tray 21 supported by four, small corner feet has a generally rectangular base 23, four sidewalls 24-27 and oppositely disposed, outwardly extending lid flanges 28 and 29. The four sidewalls 24-27 may be connected at adjacent corners, but in the preferred embodiment there is a slight corner separation. The base 23 includes numerous square-shaped steam apertures 30 arranged throughout the surface of the base 23 in a somewhat evenly spaced pattern. The lid 22 also includes a plurality of somewhat evenly spaced, square-shaped steam apertures 34.

Lid 22 includes a top covering portion 35 and front and rear down turned flanges 36 and 37. The ends are open such that lid flanges 28 and 29 will fit up against covering Portion 35 and fit between flanges 36 and 37. There is a separate slide latch mechanism disposed beneath and attached to each flange 28 and 29 which cooperates with its corresponding clearance hole 38 and 39. Anchored into covering portion 35 of lid 22 are two oppositely disposed latch pins 40 and 41. The securing of the lid to the tray involves inserting pin 40 into hole 38 and inserting pin 41 into hole 39. Thereafter, and with the lid securely clamped down onto the tray, each latch mechanism is moved into securing position such that the latch slide body locks onto its corresponding pin 40 and 41. The details of the latching mechanism are illustrated in FIG. 7.

Tray 21 is specifically configured with various apertures, slots and pins which are used to receive various holders which in turn receive and store various dental instruments and appliances (see FIG. 5). While the disclosed embodiment is directed to a dental cassette kit, similar concepts to those disclosed herein can be used for surgical cassettes and surgical cassette kits for procedures involving other portions of the human anatomy or conceivable by veterinarians for animal surgery. Once the instruments or appliances are loaded into the tray, the lid is closed and latched in place. Thereafter the cassette is wrapped in protective paper or cloth, autoclaved and stored. The enclosing lid and the fact that it is latched to the tray allows the cassette to be inverted, as would typically occur during the wrapping process without the instruments falling out of position or damaging one another. The specific manner of storing and securing the instruments and appliances in position within the cassette is described hereinafter.

Referring to FIGS. 2, 2A, 3, 4, 8 and 9 instrument-receiving devices which are installed in tray 21 are illustrated. These devices include lift-out instrument storage rack 45 (FIGS. 2 and 2A), snap-in finger mat 46 and metal storage box 47. An alternative design for rack 45 is illustrated in FIG. 8. An alternative to the metal storage box 47 is illustrated in FIG. 9.

Rack 45 sets down into one of two sets of slots in the sidewalls of the tray and the assembly technique involves the use of four outwardly-extending tabs 48, one each being disposed at each of the four corners of rack 45. Rack 45 is an open, generally-rectangular frame member having four sides, two of which (sides 49 and 50) are configured with a spaced-apart series of receiving channels 51. The receiving and outward from the receiving channels, tabs 48 channels are designed to receive dental/surgical instruments or appliances (see FIG. 5) and the seven channels 51 in side 49 are aligned with the seven channels 51 in side 50.

Rack 45 begins as a flat sheet of metal and is fabricated and notched into a four-sided frame configuration prior to bending the outer part of the four sidewalls of the frame upwardly. Each side of the frame is bent upwardly along a line roughly midway between the inner and outer edges of each sidewall of the frame. The result is a lower lip portion or shelf which is integral with each sidewall and which extends inwardly in order to provide desirable stiffening and bracing for the rack. Sides 49 and 50 are bent upwardly to a location adjacent sides 45a and 45b with a portion of each tab 48 extending beyond its corresponding and adjacent side 45a, 45b. As one alternative to this construction, it is possible for the inwardly turned metal lips 49a, 50a which are adjacent sides 49 and 50 to be turned downwardly and to be configured with oppositely facing though aligned and similarly constructed receiving channels. As will be described hereinafter, these downwardly opening receiving channels in the lower lip margin of sides 49 and 50 can in turn be used in a clamping or enclosing action against dental instruments and appliances which may be mounted in a lower rack positioned within the tray 21 directly beneath or with a slight stagger from the top rack.

Sides 24 and 25 of tray 21 each include a spaced-pair of short receiving slots 52 and 53 and a spaced-pair of long receiving slots 54 and 55. There is a total of four short receiving slots to receive the four tabs 48 of lift-out rack 45. As would be understood and as illustrated in FIG. 5, the thickness of each tab is slightly less than the width of each corresponding receiving slot and the width of each tab is sized so as to be flush with or slightly within the outer surfaces of the corresponding sidewalls 24 and 25. The depth of each short receiving slot 52 and 53 is the same and is greater than the height of tabs 48 such that the lift-out rack 45 rests in position in a substantially horizontal manner below the top edge of the tray.

The flush fit with the outer surface of the sidewall is important so that the down turned flanges 36 and 37 of the lid will not encounter any interference when the lid is assembled to the tray. Similarly, positioning the top edge of the rack below the top edge of the tray avoids any interference with covering portion 35. Notch relief areas 59 and 60 which are machined (or punched) into sidewalls 24 and 25 provide finger clearance for the handling of rack 45 and clearance for the outwardly bent tabs 61 of the FIG. 8 rack 62. Once loaded with instruments rack 45 can be easily lowered into position into the tray slots and as well lifted up out of the tray slots, without the user's hand having to contact the area of the rack sides 49 and 50. The four outwardly turned tabs 48 may also be used for the handling of rack 45 as may tabs 61 for the handling of rack 62. Handling of either rack in the area of the instruments (sides 49 and 50) would be very awkward if all seven receiving channels were being used.

In certain instances it may be desirable to separately handle and autoclave one loaded rack 45 apart from the cassette. It may also be desirable to add additional securement to the rack under various circumstances and conditions. In order to hold the instruments and appliances in position in the receiving channels 51 of rack 45, one available technique is to hook one or two rubber bands or some type of elastic strips over diagonally opposite tabs 48. If two bands are used there would preferably be a crisscross pattern. This technique may also be used for the lower rack when two racks 45 are loaded into the tray in a stacked orientation (see FIG. 6).

When the storage rack that is installed in the tray is provided with bent, outwardly extending side wall tabs 61, such as on rack 62, a rubber band or elastic strip may be hooked over the tabs 61 and into relief notches 61a and 61bso as to hold the dental instruments within the corresponding receiving channels.

The lid includes a flexible and resilient clamping bar 63 which is aligned with the interior of rack 45 and extends between sides 49 and 50 of rack 45 so as to apply a downward clamping force on the center handle portions of any dental instruments or appliances which are loaded into rack 45. Clamping bar 63 includes a rigid metal sleeve 63a which is riveted to the lid 22 and a flexible and resilient insert 63b which has the shape illustrated and is pliable enough to be able to be snapped into the formed edges of sleeve 63a. In this way a worn or damaged insert 63b can be removed and replaced. If two racks 45 are used, the clamping bar acts on the top rack. Since the instruments merely rest within the receiving channels without any type of interference fit, the turning and tumbling action of the autoclave would throw the instruments out of the rack unless retained or clamped into position. Bar 61 provides the needed clamping action. The crisscross pattern of rubber bands hooked over the tabs 48 is another way to hold the instruments in position, as is the use of tabs 61.

As should be clear from a dimensional review and comparison of the length or depth of slots 52 and 53 relative to the height of sidewalls 24 and 25 and the depth of rack 45 relative to tabs 48, a clearance space is defined between the bottom surface of rack 45 and the base 23 of tray 21. This clearance space can be used to receive one of the FIG. 3 finger mats 46 which in turn can receive one or more dental instruments or appliances as illustrated in FIG. 5. The finger mat 46 construction and installation method will be described hereinafter.

The use of the long receiving slots 54 and 55 is very similar to what has been described for the shorter receiving slots 52 and 53, with one exception. This one exception is the use of two racks 45 in a stacked configuration as illustrated in FIG. 6. The clearance space which could be used for a finger mat 46 when a single rack is installed in the shorter slot is now used for a second rack 45.

As is illustrated, the shorter and longer slots are disposed very close to one another and as should be understood, it is possible to load one rack in the shorter slots and a second rack 45 in the longer slots. It is also possible to mount both racks in the longer slot. In order to hold down the dental instruments or appliances which are loaded into the lower rack, one option is to alter inner lips 49a and 50a so as to turn them downwardly, rather than their inward orientation and provide receiving channels as has been described in connection with FIG. 2. When this is the approach that is followed, it is preferable to use the staggered arrangement of racks 45 due to the instrument clearance present in each receiving channel 51. Another option to hold down and retain the instruments stored in the lower rack is to dispose a bar or barrier strip between the bottom surface of the upper rack and the instruments in the lower rack. By the use of some resilient and compressible material, a gentle clamping force would be transmitted from the clamping bar 63, through the instruments in the top rack, through the rack and into the compressing bar disposed between the two racks.

Figure 3:
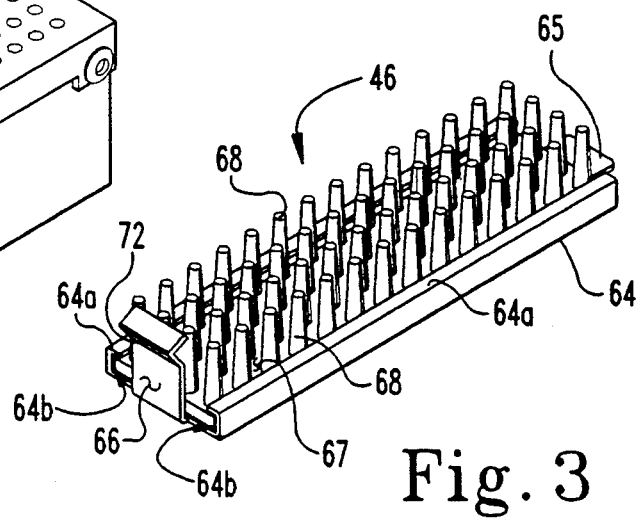
FIG. 3 is a perspective view of a finger mat designed to be installed in the FIG. 1 cassette according to the present invention.

Referring to FIG. 3, finger mat 46 is illustrated as an assembly including a metal base 64 extending at one end into a unitary tab 65 and at the opposite end into a unitary spring clip 66. Upwarding and inwardly turned base edges 64a define side receiving channels 64b. Pliably loaded into the opposite receiving channels 64b of the metal base 64 is a silicone rubber mat 67 arranged with an evenly spaced Plurality of upwardly-extending fingers 68. The mat 67 and fingers 68 are of a molded, unitary construction including four rows and fourteen columns of aligned fingers for a total of 56 gripping fingers in each mat. However, it is anticipated within the teachings of this invention that the illustrated finger mat 46 could be made substantially larger (or smaller) and in lieu of two separate mats as illustrated in FIG. 5, one larger mat could be provided, still disposed beneath rack 45. While there are in fact snap-in provisions made in the tray so as to receive two finger mats, a larger number is possible by providing the required slots in the tray.

Each finger 68 is of a gradually tapering, generally conical shape having a generally circular lateral cross section. The fingers are approximately one-half inch high from the base and the clearance spaces left between adjacent fingers are used to wedge and stabilize irregularly-shaped instruments and appliances into the mat, see FIG. 5.

While most of the conventional dental instruments such as various picks, scrapers and mirrors will fit within the receiving channels 51 of rack 45, smaller (i.e., shorter) instruments or appliances may not extend far enough to span sidewalls 49 and 50. Consequently, these items can be wedged down into the finger mat 46 allowing the silicone rubber fingers to grip around the item. The flexibility and resilient nature of silicone rubber is helpful for this Purpose as is the surface texture which having a high coefficient of friction tends to grip the dental instrument. Depending on the size and shape, more than one instrument or appliance may be nested and wedged into the finger mat 46, and as illustrated, provisions are made in the design of the tray for the use of two mats as illustrated in FIG. 5.

Each finger mat 46 has a design which in combination with the sidewalls 24 and 25 of tray 21 permits the finger mat to be installed in the tray with a snap-in/snap-out design. Tab 65 is sized to fit within lower edge slot 71 disposed at the base of the sidewall 25 just above the top surface of base 23 in tray 21. The finger mat 46 must be tilted at an upwardly inclined angle in order to initiate the insertion of tab 65 into slot 71. The next step is to push the elevated end of the mat downwardly toward base 23. As this step is performed, spring clip 66 is in interference with the inside surface of sidewall 24. The spring properties of clip 66 allow it to resiliently deflect inwardly as the finger mat is pushed closer to base 23. The degree of interference and pressure on clip 66 is substantial and increases as the finger mat 46 arrives at base 23. In a virtually simultaneous manner, as metal base 64 contacts tray base 23, the outwardly protruding rib 72 snaps into horizontal sidewall slot 73 disposed in tray sidewall 24. The center Portion of slot 73 includes an enlarged circular opening 74 in order to permit any appropriate small object such as an instrument handle or blunt instrument tip (possibly the fingertip of the user) to push inwardly and upwardly on rib 72 of clip 66 so as to disengage the rib from the slot 73 so that the corresponding finger mat can be removed. This design and the described procedure is the same for all finger mats 46.

Metal storage box 47 may either be a perforated box with a base, four sides and a hinged lid as is illustrated or this same type of construction can be provided using a screen or wire mesh material. The various openings in the sides, base and lid enable the free flow of autoclaving steam or other sterilant into and around whatever components are loaded into the storage box. The openings which are provided are not large enough to permit any small items to fall through.

Figure 4:
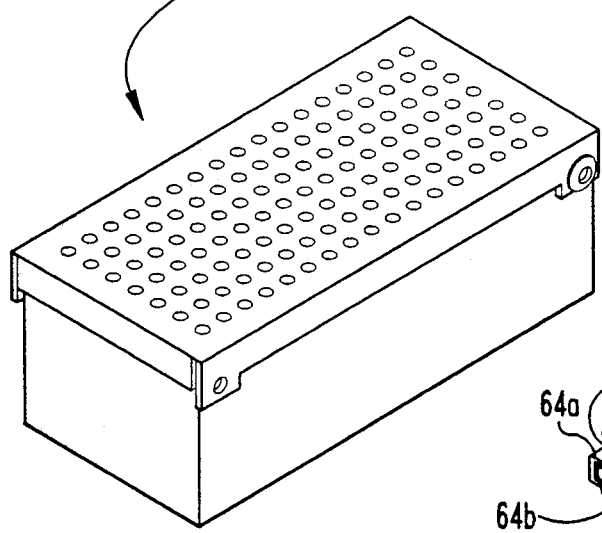
FIG. 4 is a perspective view of an instrument storage box designed to be installed in the FIG. 1 cassette according to the present invention.

As illustrated in FIG. 4 and 5, the metal storage box 47 is used to store smaller articles which are either too small for rack 45 or are not suitable for finger mat 46. For example, as illustrated, the storage box is used for articles which do not have a fixed form, such as a chain.

The metal storage box 47 fits freely into one end of tray 21. The length of the box is such that it fits closely within sides 24 and 25 which thereby restrict its movement during autoclaving. The height of the box is approximately the height of the tray, though slightly less, such that the lid of the cassette does not contact the lid of the box but is close enough so that the box lid cannot open. Even with the slight movement of the box that is allowed during the inverting and tumbling action while being autoclaved, the small articles within the box are unable to fall or slip out.

Abutment pins 77 and 78 are used to control the position and any movement of box 47 longitudinally between tray ends 26 and 27. The position of the two abutment pins 77 and 78 relative to the end sidewall 26 is close to the width of the box so that there is very little room for the box to move before engaging the abutment pins.

If there is a desire to load some type of instrument into cassette 20 which may not have a size, shape or nature which is suitable for a storage rack or finger mat and when the storage box is not required, a three-sided partition 79 may be used instead of box 47 (see FIG. 9). Partition 79 has a height, width and length similar to that of box 47 and is thus able to closely fit within tray 21 between the location of pins 77 and 78 and the end sidewall 26 of the tray.

Referring to FIG. 7 the slide latch 80 which connects the tray and lid together is illustrated. As shown in the exploded view, the latch mechanism which is riveted to the underside of tray flanges 28 and 29 includes a fixed sleeve portion 81 and disposed therein a sliding latch portion 82. The sliding latch portion has a bayonet clip design with a narrow opening 83 and an enlarged center area 84. Each pin 40 and 41 has an enlarged head and an undercut body or shoulder portion. In operation the pins extend through the clearance holes in the tray flanges and the moveable latch portion of the bayonet clip is pushed into position so as to grip around the undercut shoulder portion of each pin whereby any lifting action would force the enlarged head of the pin to abut up against the slide latch thereby preventing disengagement. When it is time to remove the lid, the slide portion is pulled back thereby freeing the lid pins and allowing the lid to be lifted.

While a specific configuration for the kit of the present invention has been provided in FIG. 5, the variations and options are many. Using one standardized cassette and tray combination, a dentist or surgeon is able to customize his own cassette kit based on the use of standard components. The illustrated components include rack 45, finger mat 46 and storage box 47. It also has been described how two lift-out racks 45 could be used and how one or two finger mats could be used as well as finger mats of different shapes and sizes.

The sizes illustrated and the reference to a "dental" cassette kit are not intended to limit the teachings of the Present invention. The present invention is applicable to various sizes of cassettes and cassettes which are intended to be used for various medical or dental procedures whether for humans or animals. Further variations and options for the standard components are also contemplated within the teachings of the present invention. For example, the length of rack 45 can vary as well as the number and spacing of receiving channels. More than two finger mats may be used, or a single, larger mat may be used. The metal storage box could be a stack of two or three smaller boxes in order to prevent a plurality of napkin chains for example from becoming entangled.

The dentist or surgeon can interchangeably customize the standard cassette and use the same tray and lid for a number of different configurations. The number of cassettes to be inventoried and stocked is less and the failure of one component, such as a torn or lost mat finger, does not cause the entire cassette to become either scrap or unacceptable for its intended use. All that is required is to snap out the damaged finger mat and snap in a new finger mat. The much more significant cost of the metal tray and lid is thereby saved by this invention feature.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An autoclavable cassette for the receipt and storage of dental and surgical instruments, said cassette comprising:
   a tray portion including a base, two oppositely disposed sidewalls and two oppositely disposed endwalls which define an open interior space, said two oppositely disposed sidewalls including means defining a plurality of rack slots and a plurality of mat slots;
   a lid portion including means for attachment to said tray portion so as to enclose said interior space;
   a lift-out instrument rack inserted into said plurality of rack slots, said instrument rack including a plurality of receiving channels for receipt of a plurality of instruments therein;
   a snap-in finger mat inserted into said plurality of mat slots, said finger mat including a base member including a tab at one end and a spring clip at the opposite end and a finger mat pad inserted into said base member, said tab fitting within one of said mat slots and said spring clip fitting within an oppositely disposed one of said mat slots.

2. The autoclavable cassette of claim 11 which further includes a second snap-in finger mat inserted into other mat slots of said plurality of mat slots, said second finger mat including a base member having a tab at one end and a spring clip at the opposite end and a finger mat pad inserted into said base member.

3. The autoclavable cassette of claim 1 which further includes a storage box having an openable lid and being designed and arranged to fit within said tray portion.

4. The autoclavable cassette of claim 1 which further include a three-sided partition designed and arranged to be placed within said tray portion so as to partition one end of said tray portion apart from the remainder of said tray portion.

5. The autoclavable cassette of claim 1 wherein said plurality of rack slots includes a total of four slots, two slots being disposed in each of said tow oppositely disposed sidewalls so as to create a four-corners pattern.

6. The autoclavable cassette of claim 5 wherein said lift-out instrument rack includes a four-sided frame and a support tab disposed at each of four corners of said frame and a pair of oppositely disposed side tabs.

* * * * *

UNITED STATES PATENT AND TRADEMARK OFFICE
CERTIFICATE OF CORRECTION

PATENT NO. : 5,279,800
DATED : January 18, 1994
INVENTOR(S) : Bernie B. Berry, Jr.

It is certified that error appears in the above-indentified patent and that said Letters Patent is hereby corrected as shown below:

In column 4, bridging lines 8 and 9, please move the phrase --and outward from the receiving channels, tabs 48-- and relocate it after "channels 51" in line 8 of column 4.

In column 10, line 8, please change "tow" to --two--.

Signed and Sealed this

Twenty-first Day of June, 1994

Attest:

BRUCE LEHMAN

Attesting Officer       Commissioner of Patents and Trademarks